US006685885B2

(12) United States Patent
Nolte et al.

(10) Patent No.: US 6,685,885 B2
(45) Date of Patent: Feb. 3, 2004

(54) BIO-OPTICAL COMPACT DIST SYSTEM

(75) Inventors: David D. Nolte, Lafayette, IN (US); Fred E. Regnier, West Lafayette, IN (US); Manoj Varma, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 77 days.

(21) Appl. No.: 10/022,670

(22) Filed: Dec. 17, 2001

(65) Prior Publication Data

US 2003/0026735 A1 Feb. 6, 2003

Related U.S. Application Data

(60) Provisional application No. 60/300,277, filed on Jun. 22, 2001.

(51) Int. Cl.[7] .............................................. G01N 21/45
(52) U.S. Cl. ........................ 422/64; 422/82.05; 436/45; 436/165; 436/518; 356/73
(58) Field of Search ................. 422/64, 82.05, 422/82.09; 436/518, 524, 528, 531, 532, 164, 165, 45; 356/72, 73, 357

(56) References Cited

U.S. PATENT DOCUMENTS

| | | | | |
|---|---|---|---|---|
| 4,537,861 A | * | 8/1985 | Elings et al. ................ 436/518 |
| 4,876,208 A | * | 10/1989 | Gustafson et al. .......... 436/531 |
| 5,413,939 A | * | 5/1995 | Gustafson et al. .......... 436/518 |
| 5,478,527 A | * | 12/1995 | Gustafson et al. ....... 422/82.11 |
| 5,545,531 A | | 8/1996 | Rava et al. |
| 5,653,939 A | | 8/1997 | Hollis et al. |
| 5,892,577 A | * | 4/1999 | Gordon ........................ 356/73 |
| 5,900,935 A | | 5/1999 | Klein et al. |
| 5,922,617 A | * | 7/1999 | Wang et al. ................. 436/518 |
| 6,110,748 A | | 8/2000 | Reber et al. |
| 6,221,579 B1 | * | 4/2001 | Everhart et al. ................ 435/5 |
| 6,312,961 B1 | * | 11/2001 | Voirin et al. ................. 436/518 |
| 6,342,349 B1 | * | 1/2002 | Virtanen ........................ 435/6 |
| 6,342,395 B1 | * | 1/2002 | Hammock et al. .......... 436/518 |
| 6,387,331 B1 | * | 5/2002 | Hunter ........................ 422/102 |
| 6,395,558 B1 | * | 5/2002 | Duveneck et al. .......... 436/172 |
| 6,496,309 B1 | * | 12/2002 | Bliton et al. ................. 359/618 |

OTHER PUBLICATIONS

Laser–Based Ultrasound Detection Using Photorefractive Quantum Wells, Applied Physics Letters, vol. 73, No. 8, Aug. 24, 1998.
Xia, Y., et al., *Non–photolithographic methods for fabrication of elastomeric stamps for use in microcontact printing.* Langmuir, 1996, vol. 12, p. 4033–4038.

(List continued on next page.)

*Primary Examiner*—Jeffrey Snay
(74) *Attorney, Agent, or Firm*—Bose McKinney & Evans LLP

(57) ABSTRACT

A device for identifying analytes in a biological sample, including a substrate having a surface lying substantially in a first plane, a plurality of targets, each having a wall lying substantially in a second plane offset from the first plane, and a receptor coating applied to one of the surface and the target walls for binding analytes present in the biological sample when the biological sample is applied to the substrate. A laser beam is sequentially directed onto each of the plurality of target, the laser being positioned relative to the substrate such that when the beam is directed onto a target, a first half of the beam is reflected back to the laser from the wall of the target and a second half of the beam is reflected back to the laser from the surface of the substrate adjacent the target. The laser combines the first and second reflected halves to produce a diffraction signal that has a first value when an analyte is not bound to the receptor coating associated with a target and a second value when an analyte is bound to the receptor coating associated with the target, thereby indicating the presence of the analyte.

23 Claims, 9 Drawing Sheets

OTHER PUBLICATIONS

Hu, J., et al., *Using soft lithography to fabricate GaAs/AlGaAs heterostructue field effect transistors.* Appl. Phys. Lett., 1997, vol. 71, p. 2020–2022.

Grzybowski, B.A., et al., *Generation of micrometer–sized patterns for microanalytical applications using a laser direct–write method and microcontact printing.* Anal. Chem., 1998, vol. 70, p. 4645–4652.

Martin, B.D., et al., *Direct protein microarray fabrication using a hydrogel stamper.* langmuir, 1998, vol. 14, p. 3971–3975.

Pompe, t., et al., *submicron contact printing on silicon using stamp pads.* Langmuir, 1999, vol. 15, p. 2398–2401.

Bietsch, A. and B. Michel, *Confromal contact and pattern stability of stamps used for soft lithography.* J. Appl. Phys., 2000, vol. 88, p. 4310–3418.

Geissler, M., et al., *Microcontact–printing chemical patterns with flat stamps.* J. Am. Chem. Soc., 2000, vol. 122, p. 6303–6304.

Sanders, G.H.W. and A. Manz, *Chip–based microsystems for genomic and proteomic analysis.* Trends in Anal. Chem., 2000, vol.19(6), p. 364–378.

Wang, J., *From DNA biosensors to gene chips.* Nucl. Acids Res., 2000, vol. 28(16), p. 3011–3016.

Hagman, M., *Doing immunology on a chip.* Science, 2000, vol. 290, p. 82–83.

Marx, J., *DNA Arrays reveal cancer in its many forms.* Science, 2000, vol. 289, p. 1670–1672.

Effenhauser, C.S., et al., *Integrated capillary electrophoresis on flexible silicone microdevices: Analysis of DNA restriction fragments and detection of single DNA molecules on microchips.* Anal. Chem., 1997, vol. 69, pp. 3451–3457.

He, B. and F.E. Regnier, Anal. Chem., 1998, vol. 70, p. 3790–3797.

Kricka, L.J., *Miniaturization of analytical systems.* Clin. Chem., 1998, vol. 44(9), p. 2008–2014.

Regnier, F.E., et al., *Chromatography and electrophoresis on chips: critical elements of future integrated, microfluidic analytical systems for life science.* Tibtech, 1999, vol. 17, p. 101–106.

Ekins, R., F. Chu, and E. Biggart, *Development of microspot multi–analyte ratiometric immunoassay using dual flourescent–labelled antibodies.* Anal. Chim. Acta, 1989, vol. 227, p. 73–96.

Ekins, R. and F.W. Chu, *Multianalyte microspot immunoassay—Microanalytical "compact Disk" of the future.* Clin. Chem., 1991, vol. 37(11), p. 1955–1967.

Ekins, R., *Ligand assays: from electrophoresis to miniaturized microarrays.* Clin. Chem., 1998, vol. 44(9), p. 2015–2030.

Gao, H., et al., *Immunosensing with photo–immobilized immunoreagents on planar optical wave guides.* Biosensors and Bioelectronics, 1995, vol. 10, p. 317–328.

Maisenholder, B., et al., *A GaAs/AlGaAs–based refractometer platform for integrated optical sensing applications.* Sensors and Actuators B, 1997, vol. 38–39, p. 324–329.

Kunz, R.E., *Miniature integrated optical modules for chemical and biochemical sensing.* Sensors and Actuators B, 1997, vol. 38–39, p. 13–28.

Dübendorfer, J. and R.E. Kunz, *Reference pads for miniature integrated optical sensors.* Sensors and Actuators B, 1997 vol. 38–39, p. 116–121.

Brecht, A. and G. Gauglitz, *recent developments in optical transducers for chemical or biochemical applications.* Sensors and Actuators B, 1997, vol. 38–39, p. 1–7.

Nolte, D.D., et al., *Adaptive Beam Combining and Interferometry using Photorefractive Quantum Wells.* J. Opt. Soc. Am. B, vol. 18, No. 2, Feb. 2001, pp. 195–205.

John, P.M.S., et al., *Diffraction–based cell detection using microcontact_printed antibody grating.* Anal. Chem., 1998, vol. 70, p. 1108–1111.

Morhard, F., et al., *Immobilization of antibodies in micropatterns for cell detection by optical diffraction.* Sensors and actuators B, 2000, vol. 70, p. 232–242.

\* cited by examiner

Priming the Land

BIO-OPTICAL COMPACT DIST SYSTEM

This application claims the benefit of U.S. Provisional Application Ser. No. 60/300,277, filed on Jun. 22, 2001, which is incorporated herein by reference.

FIELD OF THE INVENTION

The present invention generally relates to a device for detecting the presence of specific biological material in a sample, and more particularly to a laser compact disc system for detecting the presence of biological pathogens and/or analyte molecules bound to target receptors on the disc by sensing changes in the far-field diffracted intensity of the light along the optic axis of the laser caused by the pathogens and/or analytes.

BACKGROUND OF THE INVENTION

In many chemical, biological, medical, and diagnostic applications, it is desirable to detect the presence of specific molecular structures in a sample. Many molecular structures such as cells, viruses, bacteria, toxins, peptides, DNA fragments, and antibodies are recognized by particular receptors. Biochemical technologies including gene chips, immulogical chips, and DNA arrays for detecting gene expression patterns in cancer cells, exploit the interaction between these molecular structures and the receptors as described in document numbers 8–11 of the list of documents provided at the end of this specification, all of which are hereby expressly incorporated herein by reference. These technologies generally employ a stationary chip prepared to include the desired receptors (those which interact with the molecular structure under test or analyte). Since the receptor areas can be quite small, chips may be produced which test for a plurality of analytes. Ideally, many thousand binding receptors are provided to provide a complete assay. When the receptors are exposed to a biological sample, only a few may bind a specific protein or pathogen. Ideally, these receptor sites are identified in as short a time as possible.

One such technology for screening for a plurality of molecular structures is the so-called immunlogical compact disk, which simply includes an antibody microarray. [See documents 16–18]. Conventional fluorescence detection is employed to sense the presence in the microarray of the molecular structures under test. This approach, however, is characterized by the known deficiencies of fluorescence detection, and fails to provide a capability for performing rapid repetitive scanning.

Other approaches to immunological assays employ traditional Mach-Zender interferometers that include waveguides and grating couplers. [See documents 19–23]. However, these approaches require high levels of surface integration, and do not provide high-density, and hence high-throughput, multi-analyte capabilities.

SUMMARY OF THE INVENTION

The present invention provides a biological, optical compact disk ("bio-optical CD") system including a CD player for scanning biological CDs, which permit use of an interferometric detection technique to sense the presence of particular analyte in a biological sample. In one embodiment, binding receptors are deposited in the metallized pits of the CD (or grooves, depending upon the structure of the CD) using direct mechanical stamping or soft lithography. [See document 1–7]. In another embodiment, mesas or ridges are used instead of pits. Since inkpad stamps can be small (on the order of a square millimeter), the chemistry of successive areas of only a square millimeter of the CD may be modified to bind different analyte. A CD may include ten thousand different "squares" of different chemistry, each including 100,000 pits prepared to bind different analyte. Accordingly, a single CD could be used to screen for 10,000 proteins in blood to provide an unambiguous flood screening.

Once a CD is prepared and exposed to a biological sample, it is scanned by the laser head of a modified CD player which detects the optical signatures (such as changes in refraction, surface shape, or absorption) of the biological structures bound to the receptors within the pits. In general, each pit is used as a wavefront-splitting interferometer wherein the presence of a biological structure in the pit affects the characteristics of the light reflected from the pit, thereby exploiting the high sensitivity associated with interferometeric detection. For large analytes such as cells, viruses and bacteria, the interferemeter of each pit is operated in a balanced condition wherein the pit depth is $\lambda/4$. For small analytes such as low-molecular weight antigens where very high sensitivity is desirable, each pit interferometer is operated in a phase-quadrature condition wherein the pit depth is $\lambda/8$. The sensitivity can be increased significantly by incorporating a homodyne detection scheme, using a sampling rate of 1 Mbps with a resolution bandwidth of less than 1 kHz. Since pit-to-pit scan times are less than a microsecond, one million target receptors may be assessed in one second.

These and other features of the invention will become more apparent and the invention will be better understood upon review of the following specifications and accompanying drawings.

DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
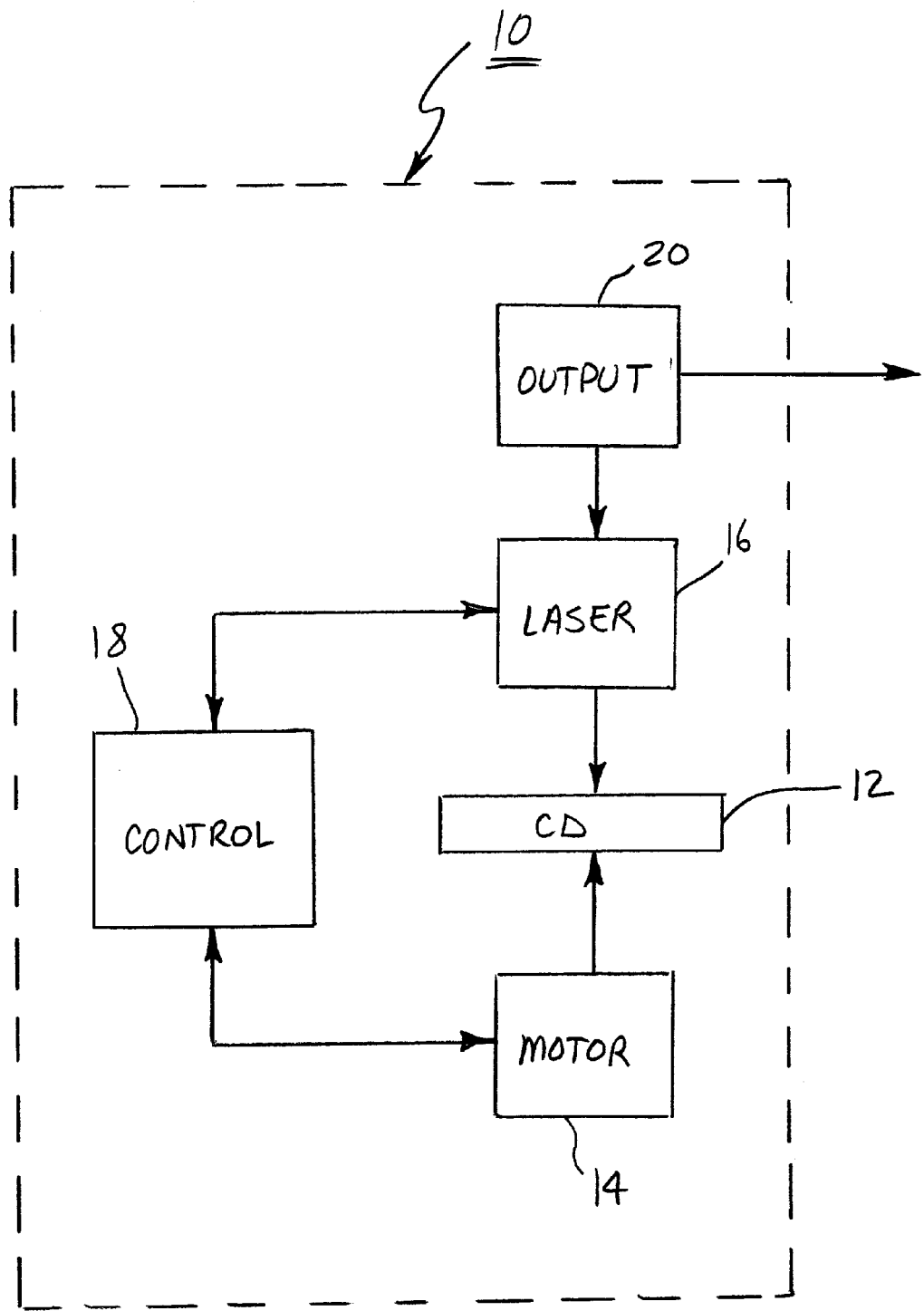
FIG. 1 is a block diagram of a bio-optical CD system according to the present invention.

Referring now to FIG. 1, a bio-optical CD system according to the present invention generally includes a CD player 10 for scanning a removable biological CD 12. CD player 10 may be a conventional, commercial CD player modified as described herein. CD player 10 includes a motor 14, a laser 16, control electronics 18, and output electronics 20. As should be apparent to one of ordinary skill in the art, the block diagram of FIG. 1 is greatly simplified, and intended merely to suggest basic components of the well-known construction of a conventional CD player. In general, control electronics 18 control the operation of laser 16 and motor 14. Motor 14 rotates CD 12. Laser 16 obtains optical information from CD 12 as is further described below. This information is then communicated to external electronics (not shown) through output electronics 20.

Figure 2:
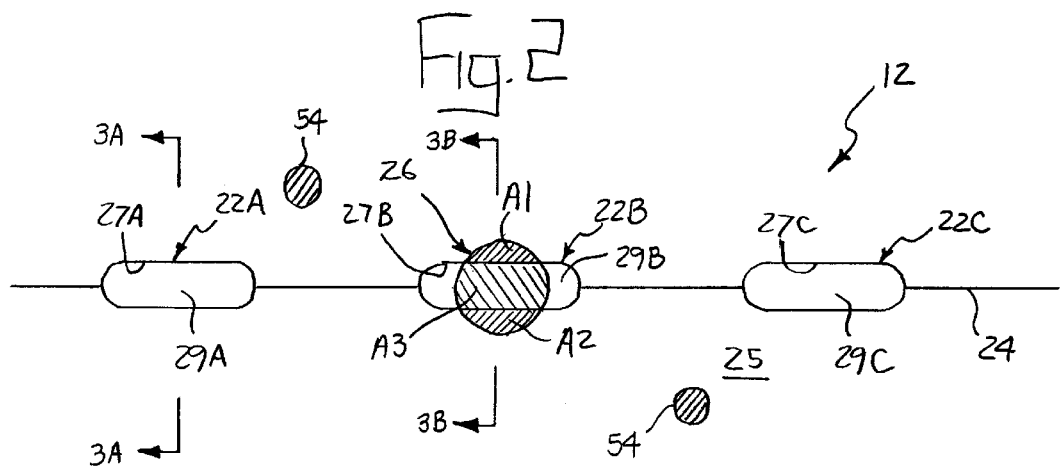
FIG. 2 is a top plan view of a portion of a CD.

As shown in FIG. 2, CD 12 includes a substrate having a plurality of pits 22A–C (three shown) arranged on a plurality of tracks 24 (one shown).). It should be understood that, while the present disclosure refers to the targets of laser 16 as "pits," one of ordinary skill in the art could readily utilize the teachings of the invention on a CD formed with targets having different shapes, such as grooves. Moreover, as is further described below, the targets could be small plateaus, or mesas formed on the surface of the CD.

Pits 22A–C and tracks 24 are separated by flat areas of the surface of CD 12 referred to as the land 25. Each pit 22 respectively includes a sidewall 27 that extends at an angle, for example, substantially perpendicularly into the body of CD 12, and a bottom wall 29 which lies in a plane below, and substantially parallel with the plane containing land 25. According to well-established principles in the art, as CD 12 rotates, pits 22 of each track 25 move under a laser beam 26 from laser 16. After each track 25 of pits 22 is scanned, laser 16 moves laser beam 26 radially relative to the center of CD 12 to the next track 25. In this manner, laser beam 26 sequentially scans each track 25 of CD 12 until the entire area of CD 12 is scanned. It should be understood, however, that if CD 12 is formed to contain a single, spiral shaped track 25, instead of the concentric circular tracks 25 described above, laser beam 26 moves in a substantially continuous radial manner to follow the spiral of the spiral shaped track 25.

The size and position of beam 26 relative to pit 22B, for example, results in 50% of the beam area (area A1 plus area A2) reflecting off land 25, and 50% of the beam area (A3) reflecting off bottom wall 29B. Thus, CD 12 is scanned using principles of a 50/50 wavefront-splitting interferometer, as further described below.

Figures 3A, 3B:
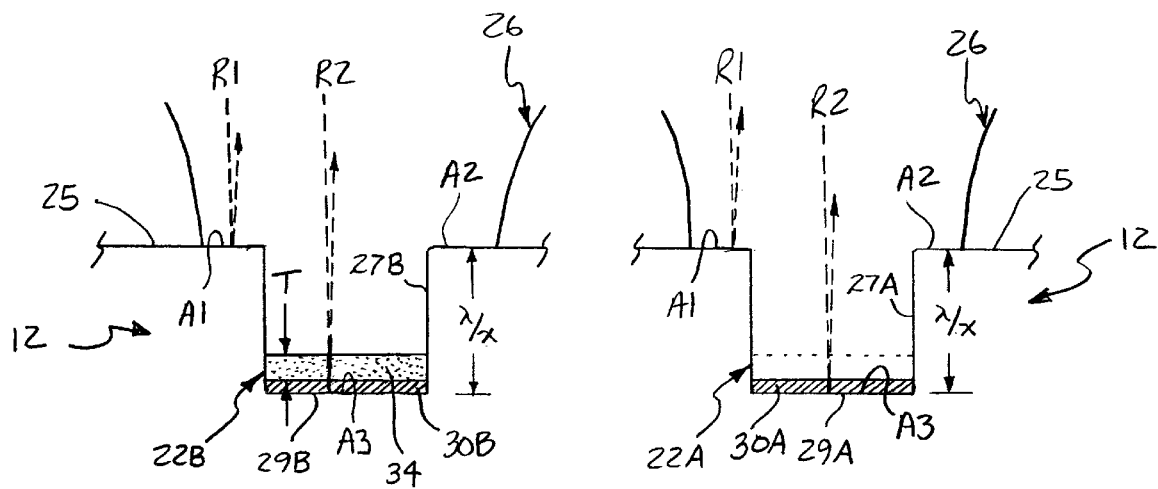
FIGS. 3A and 3B are cross-sectional views taken substantially along lines 3A—3A and 3B—3B of FIG. 2, respectively.

FIG. 3A is a cross-sectional view of pit 22A under laser beam 26. A representative light ray R1 is shown reflecting off land 25 within area A1, and a ray R2 is shown reflecting off bottom wall 29A having a thin applied antibody or receptor coating 30A. Pit 22A is shown having a depth of $\lambda/x$. Pits of conventional CDs have a depth of $\lambda/4$. On double pass (on reflection), this depth imparts a $\pi$ phase shift to the light incident in pit 22A relative to the light incident on areas A1 and A2 of land 25. In other words, because the distance traveled by ray R2 is approximately $\lambda/2$ times greater than the distance traveled by ray R1 ($\lambda/4$ down pit 22A plus $\lambda/4$ up pit 22A, ignoring the thickness of coating 30A), the reflected ray R2 appears phase shifted by one-half of one wavelength. As explained with reference to FIG. 2, the intensity of light incident on pit 22A (within area A3) is balanced by the intensity of light on land 25 (within areas A1 and A2). The equal reflected amplitudes and the $\pi$ phase difference between the light reflected from pit 22A and land 25 cause cancellation of the far-field diffracted intensity along the optic axis. The presence of pit 22A is therefore detected as an intensity drop-out as laser 16 scans over the surface of CD 12. This drop out is due to the destructive interference of the light from land 25 and pit 22A. Splitting the amplitude between pit 22A and land 25 creates the 50/50 wavefront splitting interferometer. [See document 24].

Figure 4:
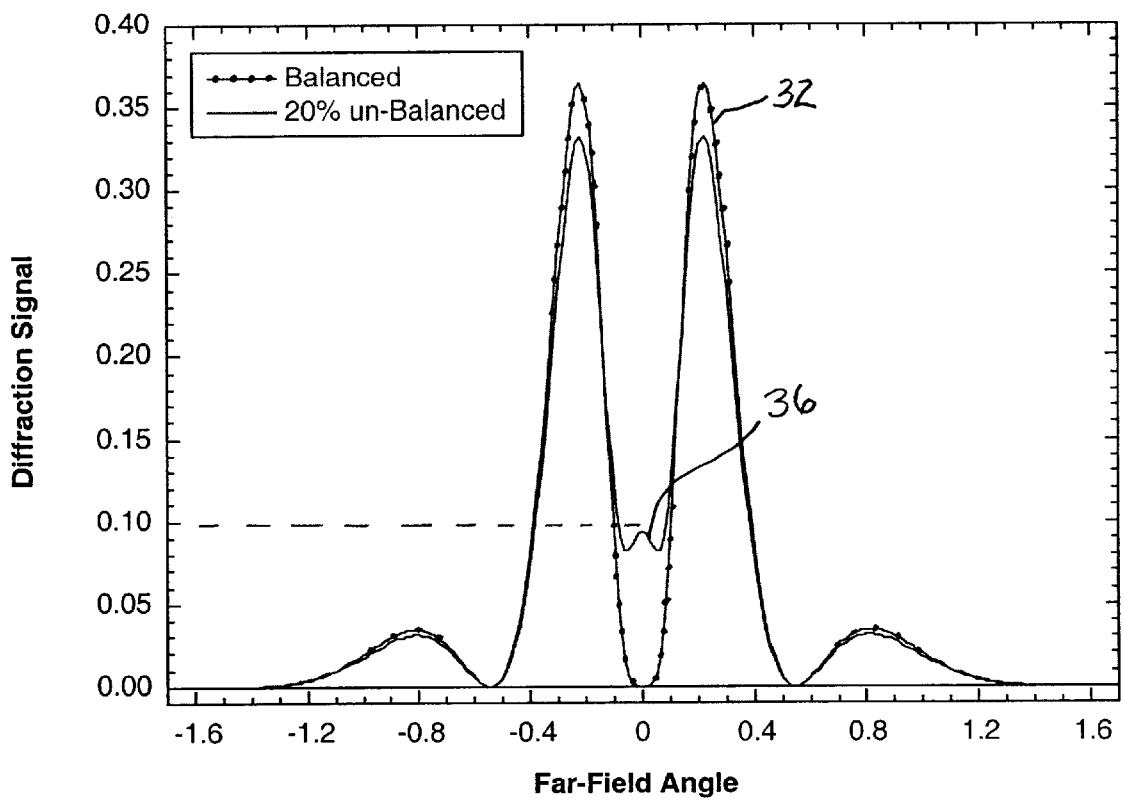
FIG. 4 is a plot of the far-field diffraction of a balanced system and a system that is 20% off the balanced condition.

The far-field diffraction of pit 22A is shown as signal 32 in FIG. 4 for the balanced condition with a $\pi$ phase difference between pit 22A and land 25. The intensity is cancelled by destructive interference along the optic axis. At finite angles, the intensity appears as diffraction orders. During immunological assays, it is common to use antibodies to bind large pathogens such as cells and bacteria. These analytes are large, comprising a large fraction of the wavelength of light. For instance, the bacterium *E coli* has a width of approximately 0.1 microns and a length of about 1 micron. While this bacterium is small enough to fit into a pit 22A–C, it is large enough to produce a large phase change from the pit 22A–C upon binding.

In this situation of a large analyte, the interferometer is best operated in the balanced condition described above. The presence of the analyte is detected directly as a removal of the perfect destructive interference that occurs in the absence of the bound pathogen as described below. It should also be understood that to improve detection sensitivity, it is possible to attach tags to bound analytes that can turn small analytes into effective large analytes. Conversely, sandwich structures can be used to bind additional antibodies to the bound analytes that can improve the responsivity of the detection.

When the balanced phase condition is removed, only partial destructive interference occurs. Referring to FIG. 3B, pit 22B is shown under beam 26. The structure of pit 22B of FIG. 3B is identical to that of pit 22A of FIG. 3A, except that receptor coating 30B has attracted a molecular structure 34 from the biological sample under test. Molecular structure 34 is shown as having a thickness T. As light ray R2 travels through thickness T of structure 34, ray 32 acquires additional phase because of the refractive index of structure 34. Specifically, since pit 22B has a depth of $\lambda/4$ (like pit 22A of FIG. 3A), and structure 34 has a thickness T, ray R2 travels in a manner that yields a phase shift of some percentage of $\lambda/2$. Assuming T is sufficiently large to result in a phase difference of $0.8*(\lambda/2)$, a diffraction signal 36 results as shown in FIG. 4. Signal 36 is approximately 10% (relative to 100% for light incident entirely on land 25) greater at a far-field diffraction angle of zero. Accordingly, one embodiment of a system of the present invention may detect the presence of particular molecular structures within a biological sample by detecting changes in diffraction signal as described above.

It should be apparent that since the system detects changes in intensity of light from one area (A3) relative to light reflected from another area (A1 plus A2), land 25 could be coated with receptor coating (not shown) instead of bottom walls 29A–C of pits 22A–C to yield the same result. In such an embodiment, molecular structure 34 binds to the coating (not shown) on land 25 adjacent pit 22A–C, thereby affecting the phase of representative light ray R1. This difference manifests itself as a change in the diffraction signal in the manner described above.

As indicated above, in an alternate embodiment of the invention, mesas are used instead of pits 22A–C. According to this embodiment, flat plateaus or mesas are formed at spaced intervals along tracks 25. Such mesas may be formed using conventional etching techniques, or more preferably, using deposition techniques associated with metalization. All of the above teachings apply in principle to a CD 12 have mesas instead of pits 22A–C. More specifically, it is conceptually irrelevant whether rays R1 and R2 acquire phase changes due to the increased travel of ray R2 into a depression or pit, or due to the reduced travel of ray R2 as it is reflected off the upper wall of a raised plateau or mesa. It is the difference between the travel path of ray R2 and that of ray R1 that creates the desired result.

Alternatively, because some cells and bacteria are comparable in size to the wavelength of light, it should also be possible to detect them directly on a flat surface uniformly coated with antibodies rather than bound in or around pits 22A–C. This has the distinct advantage that no pit (or mesa) fabrication is needed, and the targets can be patterned into strips that form diffraction gratings (see Ref. 27&28). Alternatively, it is often adequate in an immunological assay simply to measure the area density of bacteria. As laser 16 scans over the bacterium, the phase of the reflected light changes relative to land 25 surrounding the bacterium. This causes partial destructive interference that is detected as dips in the reflected intensity.

The contrast between the balanced (empty) pit and the binding pit can be large. However, high signal-to-noise-ratio (SNR) requires high intensities, which is not the case when the interferometer is balanced. Accordingly, another embodiment of the present invention employs homodyne detection that uses pit depths resulting in amplitudes from the pit and land in a condition of phase-quadrature as described below.

Figure 5:
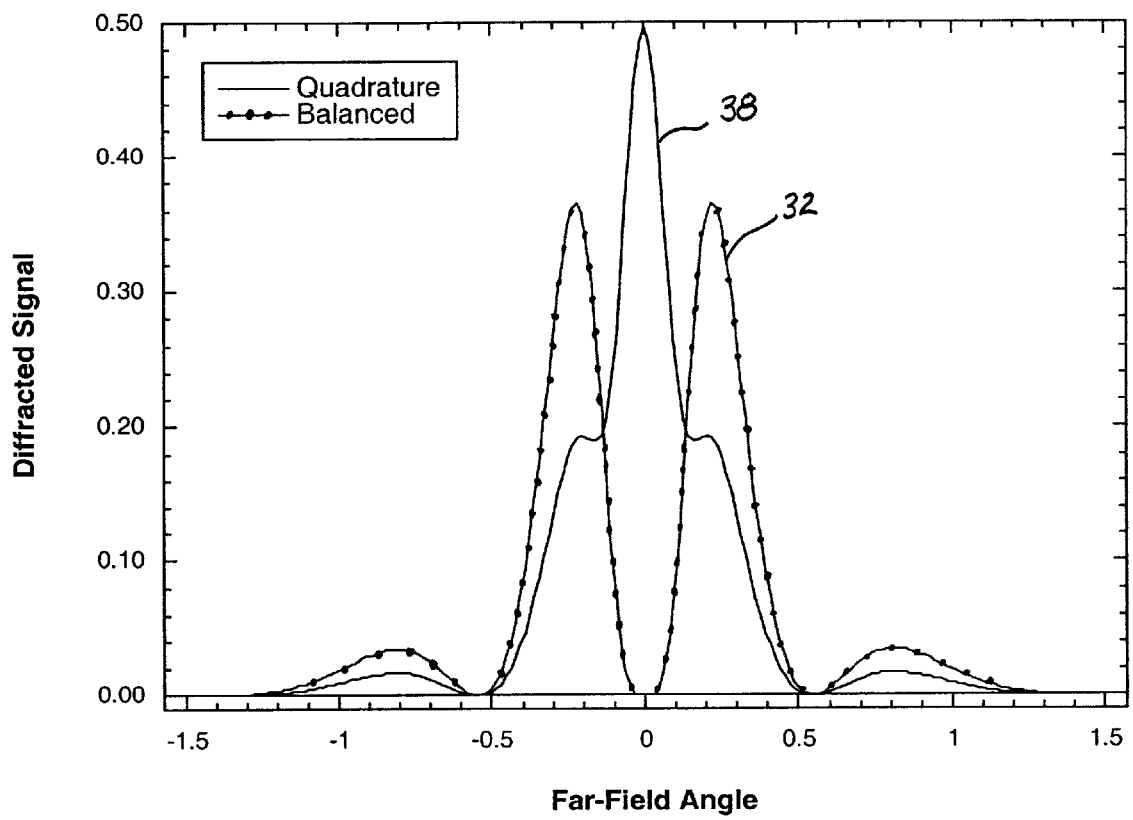
FIG. 5 is a plot of the far-field diffraction of a balanced system and a system operating in a condition of quadrature.

Phase-quadrature is attained when the two amplitudes (the light intensity reflected from pit 22A, for example, and the light intensity reflected from areas A1 and A2 of land 25 surrounding pit 22A) differ by a phase of $\pi/2$. This condition thus requires a pit depth of $\lambda/8$. It is well-known that the quadrature condition yields maximum linear signal detection in an interferometer. [See document 25]. The far-field diffraction of a pit in the condition of quadrature is shown as signal 38 in FIG. 5. In this condition, very small changes in the relative phase of the pit and land cause relatively large changes in the intensity along the optic axis. For example, a phase change of only $0.05*(\lambda/2)$ produces the same magnitude change in the diffracted signal as the relatively large phase change of $0.2*(\lambda/2)$ which resulted in signal 36 of FIG. 4. Accordingly, the condition of quadrature provides much higher sensitivity for detection of small bound molecular structures.

Figure 6:
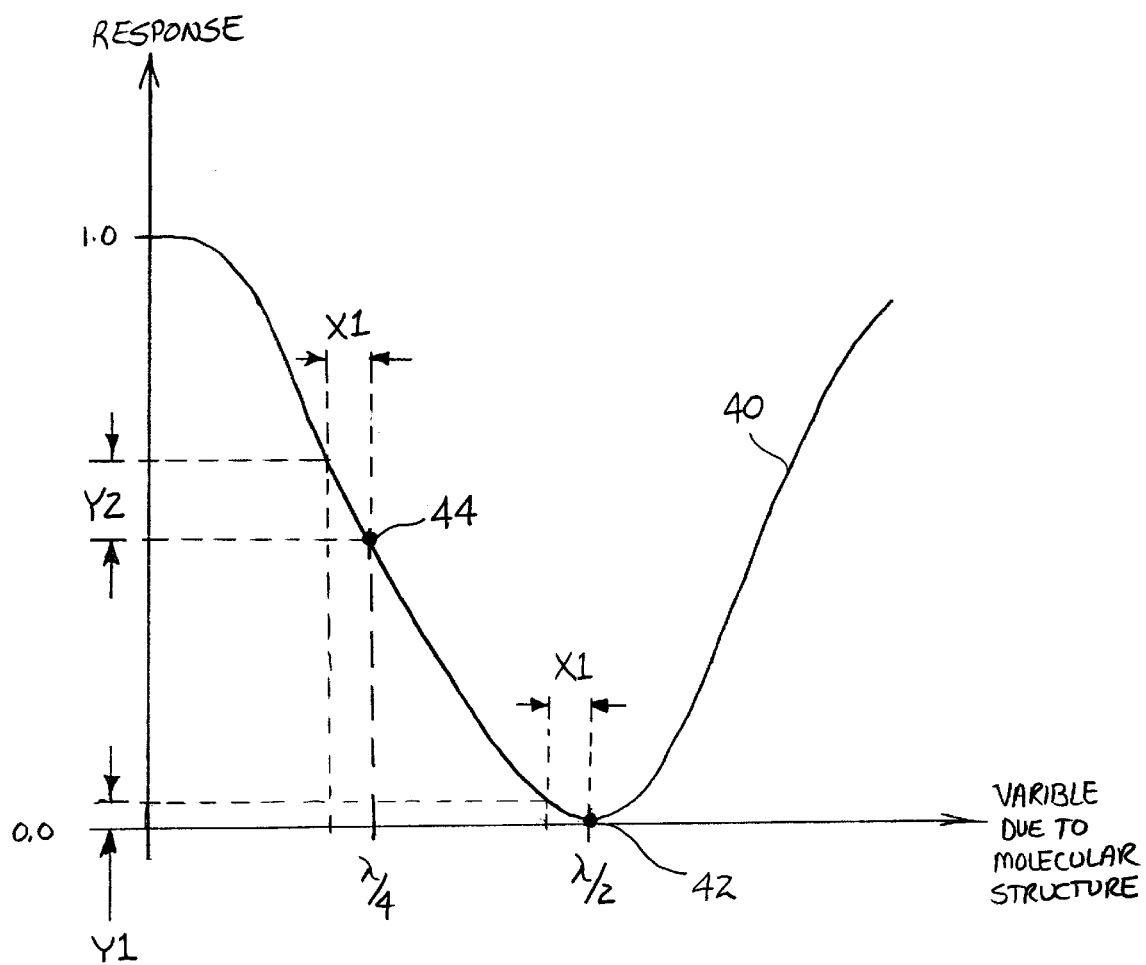
FIG. 6 is a plot of the universal response curve of interferometers.

FIG. 6 further depicts the differences in response characteristics of the two modes of operation described above. Curve 40 represents the universal response curve of all interferometers. Optical CD systems operating in a balanced condition as described above function at and around the point 42 of curve 40 corresponding to $\lambda/2$ on the x-axis of the figure. As should be apparent from the drawing, changes in the measured response (for example, light reflection) resulting from changes due to the presence of the sensed molecular structure (for example, the distance traveled by ray R2 of FIGS. 3A, 3B), are relatively small when operating about point 42 because of the low slope of curve 40. Specifically, a change of X1 along the x-axis of FIG. 6 results in a change in response of Y1.

When operating in the condition of quadrature, on the other hand, a CD system according to the present invention operates at and around the point 44 of curve 40 corresponding to $\lambda/4$ on the x-axis of FIG. 6. Clearly, this area of curve 40 yields a more responsive system because of its increased slope. As shown, the same change of X1 that resulted in a change in response of Y1 relative to point 42 yields a much greater change in response of Y2 relative to point 44.

As should be apparent from the foregoing, regardless of the depth of pits 22A–C, or even whether pits are used at all, the presence or absence of analytes creates a phase modulated signal, which conveys the screening information. If one desires to maintain a quadrature condition and its associated increased sensitivity, the technology described in U.S. Pat. No. 5,900,935, which is incorporated herein by reference, may be adapted. Instead of a phase modulated signal from an ultrasound source, the present invention so adapted provides a phase modulated signal from analytes as described above.

It is possible to derive equations describing the fundamental SNR for detection in quadrature as a homodyne detection process. The intensity along the optic axis of the detection system when it is in quadrature is given by $$I = (I_1 + I_2)\left(1 + m\cos\left(\frac{\pi}{4} + \delta\right)\right) \quad (1)$$

where $I_1$ and $I_2$ are the intensities reflected from land 25 and a particular pit 22A–C. The phase shift of the light reflected from pit 22A–C is $$\delta = \frac{4\pi}{\lambda}\Delta n d_{An} \quad (2)$$

where $\Delta n$ is the change in refractive index cause by the bound molecular structure, and $d_{An}$ is the thickness of the bound molecular structure. The contrast index m is given by $$m = \frac{2\sqrt{I_1 I_2}}{I_1 + I_2} \quad (3)$$

For ideal operation, $P_1=P_2$, $P=P_1+P_2$, and $m=1$.

For small phase excursions, the signal detected from Eq. 1 becomes $$S = \frac{P}{\sqrt{2}\,hv}m\frac{4\pi}{\lambda}\Delta n d_{An} \quad (4)$$

in terms of the total detected powers P and where hv is the photon energy. There are three sources of noise in this detection system: 1) shot noise of the light from beam 26; 2) binding statistics of the antibodies; and 3) bonding statistics of the bound analyte. The shot noise is given by $$N_{shot} = \sqrt{\frac{P}{hvBW}} \quad (5)$$

where BW is the detection bandwidth of the detection system. The noise from the fluctuations in the bound antibody is given by (assuming random statistics)

$$N_{Ab} = \frac{P}{hv}m\frac{4\pi}{\lambda}\Delta n_{Ab}\sqrt{M_{Ab}}\,d^0_{Ab} \quad (6)$$

and for the bound analyte is $$N_{An} = \frac{P}{hvBW}m\frac{4\pi}{\lambda}\Delta n_{An}\sqrt{M_{An}}\,d^0_{An} \quad (7)$$

where $M_{Ab}$ and $M_{An}$ are the number of bound antibody and analyte molecules, and $d^0_{An}$ and $d^0_{Ab}$ are the effective thicknesses of a single bound molecule given by $$Ad^0_{An} = V^0_{An} \quad (8)$$

where A is the area of pit 22A–C and $V^0_{An}$ is the molecular volume.

The smallest number of analyte molecules that can be detected for a SNR equal to unity, assuming the analyte fluctuation noise equals the shot noise, is given by the NEM (noise-equivalent molecules)

$$NEM = \frac{h\nu BW}{P}\left(\frac{\lambda}{4\pi\Delta n_{An}d^0_{An}}\right)^2 \quad (9)$$

A detected power of 1 milliwatt and a detection bandwidth of 1 Hz, assuming $\Delta n=0.1$ and $d^0_{An}=0.01$ picometer, yields a one-molecule sensitivity of $$NEM \approx 1$$

This achieves sensitivity for single molecule detection with a SNR of unity. To achieve a SNR of 100:1 would require 10,000 bound molecular structures.

An alternative (and useful) way of looking at noise is to calculate the noise-equivalent power (NEP) of the system. This is defined as the power needed for the shot noise contribution to equal the other noise contributions to the total noise. Assuming that the antibody layer thickness fluctuations dominate the noise of the system, the NEP is obtained by equating Eq. 5 with Eq. 6. The resulting NEP is $$NEP = \frac{h\nu BW}{(4\pi\Delta n_{Ab})^2 M_{Ab}}\left(\frac{\lambda}{d^0_{Ab}}\right)^2 \quad (10)$$

If an antibody layer thickness of 0.01 pm and a refractive index change of 0.1 are assumed, the resulting NEP is 1 milliwatts•molecules. If there are $10^5$ bound antibodies in a pit (or within the radius of the probe laser), then the power at which the shot noise equals the noise from the fluctuating antibody layer thickness is only $$NEP = 10 \text{ nWatts/Hz}$$

Accordingly, probe spot powers greater than 10 nW will cause the noise to be dominated by the fluctuating antibody layer thickness rather than by the shot noise. The NEP is therefore an estimate of the required power of laser 16. In this case, the power is extremely small, avoiding severe heating.

Figure 7:
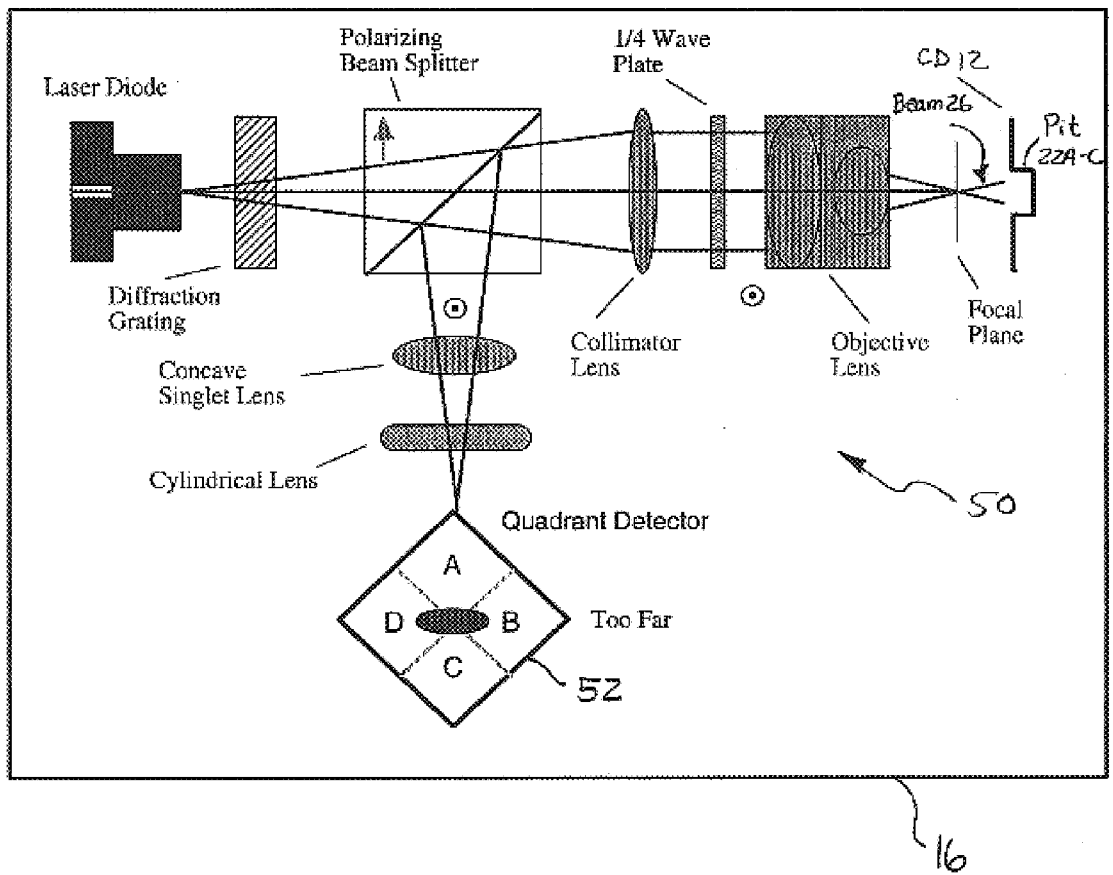
FIG. 7 is a block diagram of the optical train of a laser according to the present invention.

FIG. 7 depicts an optical train 50 included within laser 16 of FIG. 1 for detecting bound analytes. Optical train 50 is identical to to conventional optical trains currently used in commercial CD-ROM disks. Vertical tracking is accomplished "on-the-fly" using a four-quadrant detector 52 and a servo-controlled voice coil to maintain focus on the plane of spinning CD 12. Likewise, lateral tracking uses two satellite laser spots 54 (FIG. 2) with a servo-controlled voice coil to keep probe laser spot 26 on track 24. This approach uses the well-developed tracking systems that have already been efficiently engineered for conventional CD players. The high-speed real-time tracking capabilities of the servo-control systems allows CD 12 to spin at a rotation of 223 rpm and a linear velocity at the rim of 1.4 m/sec. The sampling rate is 4 Msamp/sec, representing very high throughput for an immunological assay. The ability to encode identification information directly onto CD 12 using conventional CD coding also makes the use of the CD technology particularly attractive, as patented in U.S. Pat. No. 6,110,748.

Priming the CD 12

Figure 8:
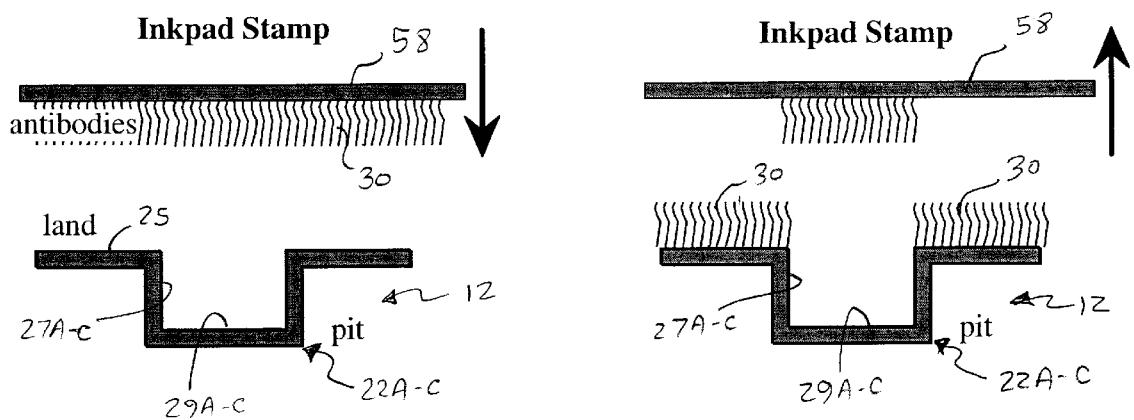
FIGS. 8 and 9 are conceptual diagrams of processes for applying receptor coatings to portions of a CD.
Figure 9:
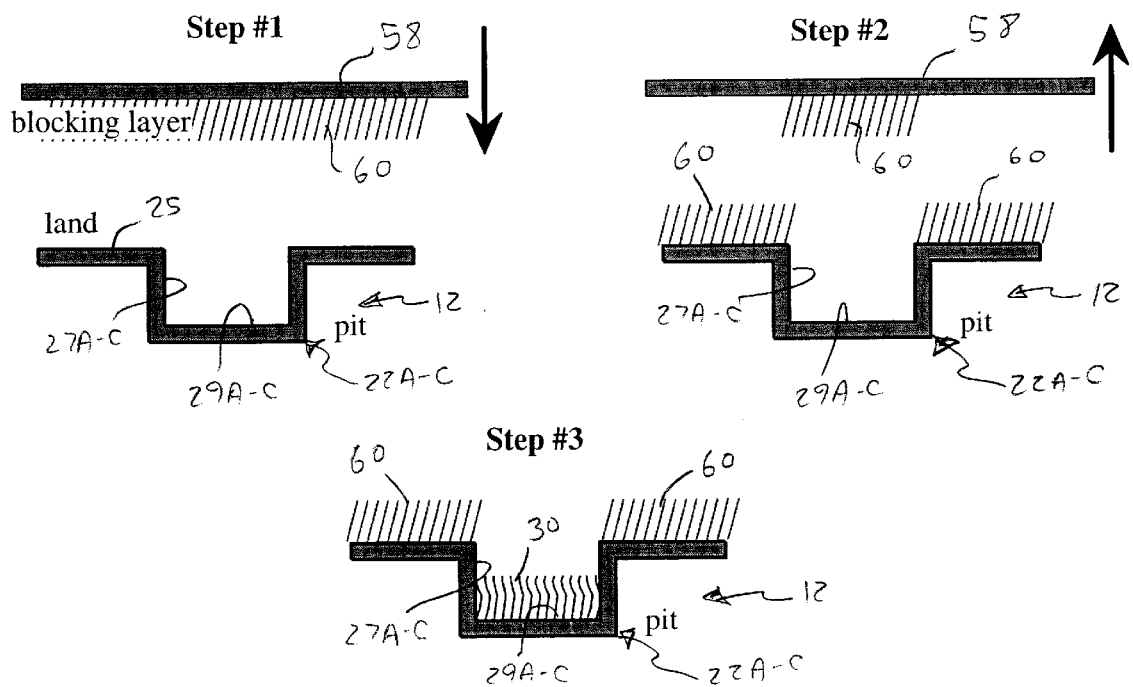

CD 12 can be charged using novel inkpad stamp technology [see documents 1–7] shown in FIGS. 8 and 9. Either land 25 or pits 22A–C can be primed with antibody layer 30. To prime land 25, the antibodies coated on the inkpad 58 attach only on land 25 that is in contact with pads 22A–C, as shown in FIG. 8. Analytes bound on land 25 are equally capable of changing the far-field diffraction as analytes bound to the pits 22A–C. Of course, as described below, the antibodies may be coated (receptor coating 30) on bottom wall 29A–C of pits 22A–C.

Referring now to FIG. 9, to prime antibodies in pits 22A–C, first a blocking layer 60 can be applied to land 25 that prevents the adhesion of antibodies 30. Later, the area is flooded with antibodies 30 that only attach in exposed pits 22A–C. Blocking layer 60 can later be removed to improve the sensitivity of the optical detection (by removing the contribution to the total noise of the detection system of the fluctuations of the thickness of blocking layer 60).

Delivery of the Biological Samples

Figure 10:
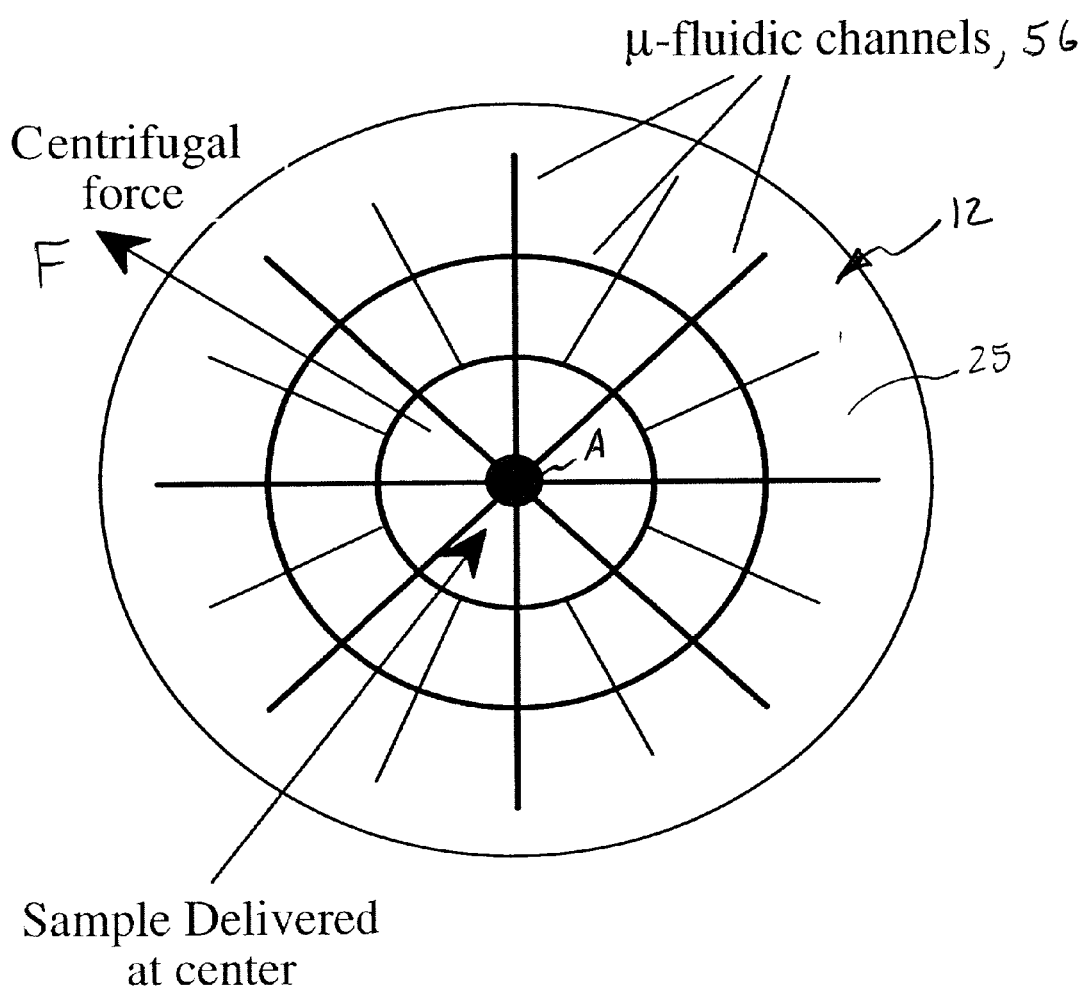
FIG. 10 is a conceptual diagram of a method for delivering a biological sample to areas of a CD.

The delivery of biological samples containing analytes to the primed areas of bio-CD 12 (i.e., pits 22A–C, land 25, or simply a flat surface of CD 12) can be accomplished using microfluidic channels 56 fabricated in CD 12, as shown in FIG. 10. Microfluidic channels 56 can plumb to all pits 22A–C. Alternatively, the biological sample can flow over land 25. The advantages in spinning CD 12 is the use of centrifugal force F to pull the fluid biological sample from the delivery area near the central axis A over the entire surface of CD 12 as an apparent centrifuge, as in U.S. Pat. No. 6,063,589. Similarly, capillary forces can be used to move the fluid through microchannels 56. This technique of biological sample distribution can use micro-fluidic channels 56 that are lithographically defined at the same time CD pits 22A–C are defined.

What is claimed is:

1. A device for identifying analytes in a biological sample, including: a substrate having a plurality of pits, each of the pits extending into the substrate from a land area to a bottom wall having a receptor coating thereon for binding analytes upon application of the biological sample to the substrate;
   a laser including a beam that is sequentially directed into each of the plurality of pits;
   wherein when an analyte is not bound to a receptor coating of a pit, a portion of the beam reflected off the coating is combined with a portion of the beam reflected off the land area to produce a first diffraction signal, and when an analyte is bound to the coating, a portion of the beam reflected off the bound analyte is combined with a portion of the beam reflected off the land area to produce a second diffraction signal, thereby indicating the presence of the analyte.

2. The device of claim 1 wherein the land areas of the plurality of pits lie in a first plane, and the bottom walls of the pits lie in a second plane at a distance from the first plane.

3. The device of claim 2 wherein the distance is approximately one-eighth the distance of a wavelength of the beam.

4. The device of claim 2 wherein the distance is approximately one-fourth the distance of a wavelength of the beam.

5. The device of claim 1 wherein the device functions as a homodyne optical detector operating in quadrature.

6. The device of claim 1 wherein the substrate is a compact disk.

7. The device of claim 1 further including a motor for rotating the substrate.

8. The device of claim 1 wherein the portion of the beam reflected off the coating is approximately fifty percent of the total area of the beam that is reflected off the substrate.

9. The device of claim 1 wherein the portion of the beam reflected off the coating has a first intensity and the portion of the beam reflected off the land area has a second intensity, the first intensity being phase shifted relative to the second intensity.

10. The device of claim 9 wherein the phase shift is approximately $\pi/2$.

11. The device of claim 9 wherein the phase shift is greater than zero and less than $\pi$.

12. A device for identifying analytes in a biological sample, including:
- a substrate having a surface lying substantially in a first plane, a plurality of targets offset vertically from the substrate surface, each of the targets having wall lying substantially in a second plane, and a receptor coating applied to one of the surface and the walls of the targets for binding analytes present in the biological sample when the biological sample is applied to the substrate;
- a laser for sequentially directing a beam at each of the plurality of targets, the laser being positioned relative to the substrate such that when the beam is directed at a target, a first half of the beam is reflected back to the laser from the target wall and a second half of the beam is reflected back to the laser from the surface of the substrate adjacent the target, the laser combining the first and second reflected halves to produce a diffraction signal;
- wherein the diffraction signal has a first value when an analyte is not bound to the receptor coating associated with a target and a second value when an analyte is bound to the receptor coating associated with the target, thereby indicating the presence of the analyte.

13. The device of claim 12 wherein each target functions as an independent interferometer.

14. A device for identifying analytes in a biological sample, including:
- a substrate having a plurality of mesas formed thereon, each of the mesas extending above the substrate from a land area and having an upper surface with a receptor coating thereon for binding analytes upon application of the biological sample to the substrate;
- a laser including a beam that is sequentially directed onto each of the plurality of mesas;
- wherein when an analyte is not bound to a receptor coating of a mesa, a portion of the beam reflected off the coating is combined with a portion of the beam reflected off the land area to produce a first diffraction signal, and when an analyte is bound to the coating, a portion of the beam reflected off the bound analyte is combined with a portion of the beam reflected off the land area to produce a second diffraction signal, thereby indicating the presence of the analyte.

15. The device of claim 14 wherein the land areas of the plurality of mesas lie in a first plane, and the upper surfaces of the mesas lie in a second plane at a distance from the first plane.

16. The device of claim 15 wherein the distance is approximately one-eighth the distance of a wavelength of the beam.

17. The device of claim 15 wherein the distance is approximately one-fourth the distance of a wavelength of the beam.

18. The device of claim 14 wherein the device functions as a homodyne optical detector operating in quadrature.

19. The device of claim 14 wherein the substrate is a compact disk.

20. The device of claim 14 wherein the portion of the beam reflected off the coating is approximately fifty percent of the total area of the beam that is reflected off the substrate.

21. The device of claim 14 wherein the portion of the beam reflected off the coating has a first intensity and the portion of the beam reflected off the land area has a second intensity, the first intensity being phase shifted relative to the second intensity.

22. The device of claim 21 wherein the phase shift is approximately $\pi/2$.

23. The device of claim 21 wherein the phase shift is greater than zero and less than $\pi$.

* * * * *

UNITED STATES PATENT AND TRADEMARK OFFICE
CERTIFICATE OF CORRECTION

PATENT NO.   : 6,685,885 B2
DATED        : February 3, 2004
INVENTOR(S)  : Nolte et al.

It is certified that error appears in the above-identified patent and that said Letters Patent is hereby corrected as shown below:

<u>Title page, Item [54] and Column 1, line 1,</u>
Title , please change "DIST" to -- DISK --

Signed and Sealed this

Twenty-fifth Day of May, 2004

JON W. DUDAS
*Acting Director of the United States Patent and Trademark Office*